United States Patent [19]

Fryer et al.

[11] 4,111,934

[45] Sep. 5, 1978

[54] 1,5-BENZODIAZEPIN-4-ONES

[75] Inventors: Rodney Ian Fryer, North Caldwell; Leo Henryk Sternbach, Upper Montclair; Armin Walser, West Caldwell, all of N.J.

[73] Assignee: Hoffmann-La Roche Inc., Nutley, N.J.

[21] Appl. No.: 861,084

[22] Filed: Dec. 15, 1977

Related U.S. Application Data

[62] Division of Ser. No. 371,442, Jun. 19, 1973, abandoned.

[51] Int. Cl.² .................. C07D 243/12; C07D 487/04
[52] U.S. Cl. ...................... 260/239.3 B; 260/239.3 T; 424/269

[58] Field of Search .................. 260/239.3 B

[56] References Cited

U.S. PATENT DOCUMENTS 4,075,202  2/1978  Moffett ................. 260/239.2 T

*Primary Examiner*—Henry R. Jiles
*Assistant Examiner*—Robert T. Bond
*Attorney, Agent, or Firm*—Samuel L. Welt; George M. Gould; Frank P. Hoffman

[57] ABSTRACT

Novel 1,5-benzodiazepin-4-one derivatives, bearing between the 1,2-positions a triazolo ring, as disclosed. These 1,2-triazolo-1,5-benzodiazepin-4-ones are useful as muscle-relaxant, anti-convulsant and sedative agents.

1 Claim, No Drawings

1,5-BENZODIAZEPIN-4-ONES

This is a division of application Ser. No. 371,442 filed June 19, 1973, now abandoned.

DETAILED DESCRIPTION OF THE INVENTION

The present invention relates to 1,2-triazolo-1,5-benzodiazepin-4-one derivatives. The invention further comprehends processes for making these novel benzodiazepines and novel intermediates employed in these processes.

More specifically, the compounds of the present invention are selected from the group consisting of compounds of the general formula

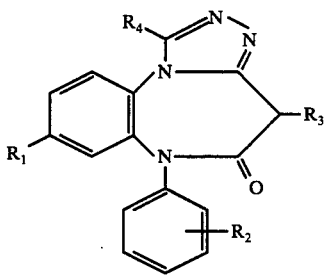

wherein $R_1$ is selected from the group consisting of hydrogen, halogen, lower alkyl, lower alkoxy, trifluoromethyl, nitro and amino; $R_2$ signifies hydrogen, halogen or lower alkoxy; $R_3$ signifies hydrogen or lower alkyl; $R_4$ signifies hydrogen or lower alkyl and the pharmaceutically acceptable acid addition salts thereof.

As used herein, the term "lower alkyl" refers to straight and branched chain hydrocarbon groups containing from 1 to 7, preferably from 1 to 4 carbon atoms, such as, for example, methyl, ethyl, propyl, isopropyl, t-butyl and the like. The term "halogen" refers to all four forms thereof, i.e. bromine, chlorine, fluorine and iodine unless specified otherwise. The term "lower alkoxy" comprehends a lower alkyl group having an oxygen function substituted therein, such as methoxy, ethoxy, propoxy and the like.

A preferred class of compounds falling within the scope of formula I above are those wherein $R_1$ signifies nitro or halogen, preferably chlorine or iodine, $R_2$ is hydrogen or halogen, preferably chlorine or fluorine, and is located in the 2-position of the 6-phenyl ring, and $R_3$ is hydrogen, i.e. compounds of the formula

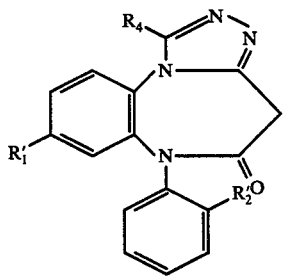

wherein $R_1'$ signifies nitro or halogen, preferably chlorine or iodine; $R_2'$ signifies hydrogen or halogen, preferably chlorine or fluorine; $R_4$ is as described above and the pharmaceutically acceptable acid addition salts thereof.

In the compounds of formula I above, when $R_3$ is lower alkyl, it is preferably methyl and when $R_4$ is a lower alkyl group, it is preferably a methyl group.

The most preferred compounds of formula I above are:
8-chloro-4,6-dihydro-1-methyl-6-phenyl-5H-S-triazolo[4,5-a][1,5]benzodiazepin-5-one;
8-nitro-4,6-dihydro-1-methyl-6-phenyl-5H-S-triazolo[4,5-a][1,5]benzodiazepin-5-one;
8-chloro-4,6-dihydro-6-phenyl-5H-S-triazolo[4,5-a][1,5]benzodiazepin-5-one;
8-chloro-4,6-dihydro-1-methyl-6-(2-fluorophenyl)-5H-S-triazolo[4,5-a][1,5]benzodiazepin-5-one; and
8-iodo-4,6-dihydro-1-methyl-6-phenyl-5H-S-triazolo[4,5-a][1,5]benzodiazepin-5-one.

Also included within the purview of the present invention are the acid addition salts of the novel compounds of formula I above. More particularly the compounds of formula I above form acid addition salts with pharmaceutically acceptable organic or inorganic acids such as hydrochloric acid, hydrobromic acid, nitric acid, sulfuric acid, acetic acid, formic acid, succinic acid, maleic acid, paratoluene sulfonic acid and the like.

The compounds of formula I above are useful as anticonvulsants, muscle relaxants and sedatives. Thus, these compounds can be used as medicaments. For example, they can be used in the form of pharmaceutical preparations which contain them in admixture with a pharmaceutical organic or inorganic carrier material which is suitable for enteral or parenteral application such as, for example, water, gelatin, lactose, starches, magnesium stearate, talc, vegetable oils, gum arabic, polyalkylene glycols, vaseline, etc. The pharmaceutical preparations can be prepared in solid form (e.g. as tablets, dragees, suppositories, capsules) or in liquid form (e.g. as solutions, suspensions or emulsions). They may be sterilized and/or contain additives such as preserving, stablizing, wetting or emulsifying agents, salts varying the osmotic pressure or buffers. They can also contain other therapeutically valuable substances.

The compounds of formula I above can be administered at dosages adjusted to individual requirements and fitted to the pharmaceutical exigencies of the situation. Convenient pharmaceutical dosages are in the range of from about 2 milligrams to about 200 milligrams per day.

The useful anticonvulsant activity of the compounds of this invention is shown in warm-blooded animals utilizing the standard antimetrazole test. In the antimetrazole test, a compound is administered orally to groups of four mice at various dose levels. One hour later metrazole is administered subcutaneously and the animals are observed for protection from convulsive seizures. Results are recorded as the number of animals protected against convulsions. The dose at which 50% of the animals are protected from convulsive seizures is expressed as the $ED_{50}$. Following these test procedures, the compound 8-chloro-4,6-dihydro-1-methyl-6-phenyl-5H-S-triazolo-[4,5-a][1,5]benzodiazepin-5-one shows an $ED_{50}$ of 8.4 ±1.4 milligrams per kilogram, indicating that this compound exhibits anticonvulsant activity.

The sedative and muscle relaxant activity of the compounds of the invention is shown using the standard foot shock test. In this test a pair of mice is confined under a 1 liter beaker placed on a grid which presents shock to the feet. At least five fighting episodes are elicited in a 2-minute period. Pairs of mice are marked and pre-treated 1 hour prior to a second shocking. Varying dose intervals are utilized up to a maximum of 10 milligrams per kilogram. At the 100% blocking dose, three out of three pairs must be blocked from fighting. The measurements are made at the dose level at which 100% blocking is observed and the results are expressed as the dose in milligrams per kilogram which block the fighting response for 1 hour. Following these test procedures, 8-chloro-4,6-dihydro-1-methyl-6-phenyl-5H-S-triazolo[4,5-a][1,5]benzodiazepin-5-one exhibited $PD_{50}$ of 100 milligrams per kilogram, indicating that this compound exhibits sedative and muscle relaxant activity.

The novel compounds of formula I above may be prepared following a variety of synthetic routes. In one such process aspect the known 1,5-benzodiazepin-2,4-dione of the formula

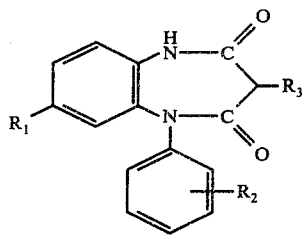

wherein $R_1$, $R_2$ and $R_3$ are as described above is converted to the corresponding 2-amino-1,5-benzodiazepin-4one of the formula

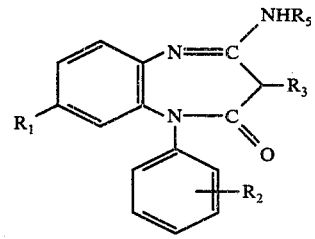

wherein $R_1$ through $R_3$ are as described above and $R_5$ signifies lower alkyl.

The conversion of the dione of formula II to the 2-amino-substituted benzodiazepine of formula III is effected by first reacting the formula II compound with a halogenating agent. Suitable halogenating agents for this purpose include phosphorus pentachloride, stannous tetrachloride, titanium tetrachloride and the like with titanium tetrachloride being the preferred halogenating agent. Following treatment with the halogenating agent, the resulting product, activated in the 2-position, is then treated with a primary amine of the formula $$H N—R_5 \qquad IV$$

wherein $R_5$ is as described above.

The conversion of the compound of formula II to the corresponding 2-amino compound of formula III is preferably effected in the presence of an inert organic solvent. Suitable solvents for this purpose include aromatic hydrocarbons such as benzene and toluene, chlorinated hydrocarbons such as methylene chloride and carbon tetrachloride and ethers such as tetrahydrofuran. Temperature is not a critical factor to the performance of this reaction and temperatures in the range of from below 0° to the reflux temperature of the reaction medium can be employed.

In the compounds of formulae III and IV above, the $R_5$ substituent, which is a lower alkyl group, is preferably a methyl group.

The 2-amino substituted benzodiazepine of formula III above is then reacted with nitrous acid to yield the corresponding 1,5-benzodiazepin-4-one bearing an N-nitrosoalkylamino substituent in the 2-position, i.e. a compound of the formula

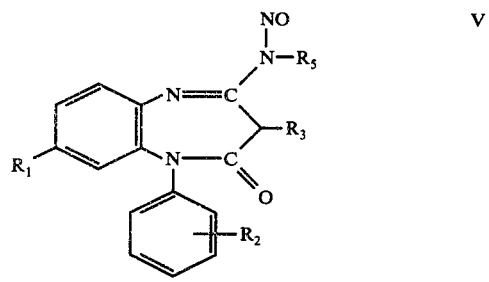

wherein $R_1$, $R_2$, $R_3$ and $R_5$ are as described above.

The compounds of formula V above are novel and hence constitute a part of the present invention.

It is expedient to introduce the nitrous acid into the reaction zone by first dissolving the compound of formula III in a suitable solvent and then adding to the so-formed solution an alkali metal nitrite, preferably sodium nitrite. Suitable solvents for this purpose include alcohols such as methanol, ethanol and the like and lower alkanoic acids such as acetic acid, propionic acid and the like. Alternately, the nitrous acid can be provided by adding to the solution a lower alkyl nitrite such as methyl, ethyl or amylnitrite.

The treatment of the compound of formula III above with nitrous acid in either of the above discussed embodiments is permitted to proceed, at above or below room temperature, preferably at room temperature or below, to the desired compound of formula V above. In the most preferred aspect, temperatures from about −5° to about 25° C. are utilized.

The so-obtained nitroso derivative of formula V is then treated with hydrazine, preferably anhydrous hydrazine, to yield a compound of the formula

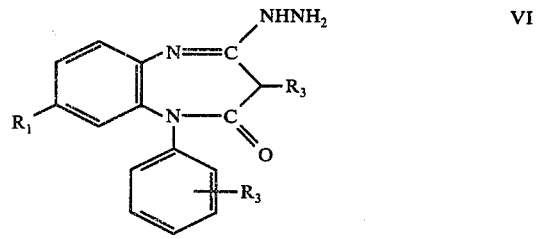

wherein $R_1$, $R_2$ and $R_3$ are as described above.

The reaction of the compound of formula V with hydrazine is preferably effected in the presence of an inert organic solvent. Suitable solvents include ethers, such as diethyl ether, tetrahydrofuran and the like, lower alkanols such as methanol, ethanol, propanol and the like or mixtures of the two. Temperature is not a critical aspect of this process step and temperatures at room temperature or above or below room temperature can be employed. Preferably temperatures in the range of from about 20° C. to about 60° C. are suitable for the purposes of this reaction.

The so-obtained compounds of formula VI above need not be isolated, but can be converted without isolation into the desired compounds of formula I by treating said intermediate with a tri-lower alkyl-ortho-lower alkanoylate. Examples of such ortho esters suitable for the purposes of the present invention include trimethyl-orthoacetate, triethyl-orthoacetate, triethyl-orthoformate, triethyl-orthopropionate, triethyl-orthobutyrate and the like. As should be evident from the course of the reaction, the alkane portion of the ortho ester determines the nature of the $R_4$ substituent. Thus, for example, if triethyl-orthoformate is used, the $R_4$ substituent will be hydrogen, whereas if triethyl-orthoacetate is employed, the $R_4$ substituent will be a methyl group.

The reaction of the compound of formula VI above with a tri-lower alkyl-ortho-lower alkanoylate is preferably effected in the presence of an inert organic solvent. Suitable solvents for the purposes of this process aspect include lower alkanols such as methanol, ethanol, propanol and the like, ethers such as tetrahydrofuran, diethylether and the like, dimethylsulfoxide and dimethylformamide. Temperature is not a critical aspect to the successful performance of this reaction. Thus temperatures at room temperature or above can be employed. Temperatures from about 30° to about the reflux temperature of the reaction mixture are preferred, with reflux conditions being the most preferred.

It is expedient to carry out the above-discussed reaction in the presence of an acid promoter. Any strong acids, such as a hydrohalic acid, for example hydrochloric acid, sulfuric acid or paratoluene sulfonic acid, would be suitable for use as the acid promoter.

In an alternate synthetic approach, the compounds of formula I above can be prepared directly from the corresponding 2-amino intermediate of formula III or the 2-nitroso intermediate of formula V by treating either intermediate with a lower alkanoyl hydrazide. Representative of the lower alkanoyl hydrazides which can be used in this process aspect are acetyl hydrazide, propionyl hydrazide, butyryl hydrazide and the like. This reaction between either a compound of formula III or V above and a lower alkanoyl hydrazide is expediently effected in the presence of an inert organic solvent. Suitable solvents include lower alkanols, such as ethanol, butanol and the like, dimethylformamide, ethers such as diglyme and methoxyethanol, or ethylene glycol. This process aspect is preferably effected at elevated temperatures, most preferably at about the reflux temperature of the reaction medium.

In a further process aspect, the compounds of formula I above can be prepared by reacting the 2-nitrosobenzodiazepine of formula V above with a lower alkanol. This reaction, which is carried out in the presence of either a tertiary amine, such as triethylamine, or the alcoholate corresponding to the lower alkanol employed, results in the preparation of the 2-lower alkoxy derivative of the formula

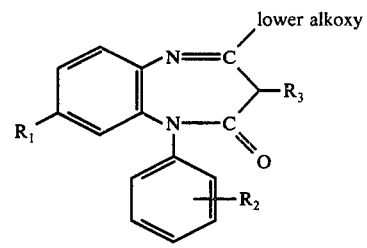

wherein $R_1$-$R_3$ are as described above. Suitable lower alkanols of the present purposes include methanol, ethanol and the like. If the reaction between the compound of formula V and the alcohol is effected in the presence of the corresponding alcoholate, systems such as methanol/sodium methylate, ethanol/sodium ethylate and the like can be employed. Temperature is not critical to the process step so that temperatures above or below room temperature are appropriate.

The thus-obtained 2-alkoxy derivative of formula VII above is then converted to the desired end product of formula I by treating said compound with a lower alkanoyl hydrazide. The reaction conditions described above for the reaction between the 2-amino intermediate of formula III and the lower alkanoyl hydrazide are equally applicable here.

The following examples are illustrative but not limitative of the present invention. All temperatures are stated in degrees Centigrade.

EXAMPLE 1

Preparation of 7-chloro-3,5-dihydro-2-methylamino-5-phenyl-4H-1,5-benzodiazepin-4-one A suspension of 14.3g (0.05 mol) of 7-chloro-5-phenyl-1,2,3,5-tetrahydro-4H-1,5-benzodiazepin-2,4-dione in 1l of tetrahydrofuran and 200 ml of benzene was saturated with methylamine. A solution of 11.5 g (0.06 mol) of titanium tetrachloride in 200 ml of benzene was added at 0° through a dropping funnel. After stirring at 0° to 10° for 15 min, the mixture was heated to reflux for 1 ½ hrs. It was then partitioned between water and benzene. The benzene layer was separated, dried and evaporated. Crystallization of the residue form methylene chloride/hexane yielded the above-named product, mp 215°–217°.

EXAMPLE 2

Preparation of 7-chloro-3,5-dihydro-2-(N-nitrosomethylamino)-5-phenyl-4H-1,5-benzodiazepin-4-one A mixture of 6 g (0.02 mol) of 7-chloro-3,5-dihydro-2-methylamino-5-phenyl-4H-1,5-benzodiazepin-4-one, 25 ml of glacial acetic acid and 1.75 g (0.025 mol) of sodium nitrite was stirred stirred at 10°–20° for 1 hr. The reaction mixture was diluted with ice and water and stirred for another 15 min. The precipitated material was collected and dissolved in methylene chloride. The solution was washed with sodium bicarbonate solution, dried over sodium sulfate and evaporated. Crystallization from methylene chloride/hexane yielded the above-named product as yellow crystals, with mp 120°–125°. For analysis it was recrystallized like form methylene chloride/hexane, mp. 122°–125°.

EXAMPLE 3

Preparation of 8-chloro-4,6-dihydro-1-methyl-6-phenyl-5H-S-triazolo [4,5-a] [1,5] benzodiazepin-5-one Hydrazine, 3 ml, was added to a solution of 3.3 g (0.01 mol) of 7-chloro-3,5-dihydro-2-(N-nitrosomethylamino)-5-phenyl-4H-1,5-benzodiazepin-4-one in 50 ml of tetrahydrofuran and 20 ml of methanol. After sitting at room temperature for 2 hrs., the solvents were removed under reduced pressure. The residue was partitioned between methylene chloride and water. The organic layer was dried and evaporated to leave 3.1 g of crude 7-chloro-3,5-dihydro-2-hydrazine-5-phenyl-4H-1,5-benzodiazepin-4-one. This material was mixed with 100 ml of ethanol, 3 ml of triethylorthoacetate and 0.1 g of p-toluene sulfonic acid. The mixture was refluxed for 1 hr. The residue obtained after evaporation of the solvent was partitioned between methylene chloride and sodium bicarbonate solution. The organic layer was dried and evaporated. Crystallization of the residue from ethylacetate yielded the above-named product. For analysis it was recrystallized from ethylacetate, mp. 298°–300°.

EXAMPLE 4

Preparation of 8-chloro-4,6-dihydro-1-methyl-6-phenyl-5H-S-triazolo [4,5-a] [1,5] benzodiazepin-5-one A mixture of 0.5 g of 7-chloro-3,5-dihydro-2-methylamino-5-phenyl-4H-1,5-benzodiazepin-4-one and 1.5 g of acetylhydrazide was heated to reflux (220°–225°) for 3 min. The cooled mixture was partitioned between water and methylene chloride. The methylene-chloride layer was dried and evaporated. Chromotography of the residue on 10 g of silica gel with 10% ethanol in methylene chloride and crystallization of the homogenous portions from ethylacetate yielded the above-named product, mp. 298°–300°.

EXAMPLE 5

Following the procedure set forth in Example 1 above, from 5-phenyl-1,2,3,5-tetrahydro-4H-1,5-benzodiazepin-2,4-dione there can be prepared 3,5-dihydro-2-methylamino-5-phenyl-4H-1,5-benzodiazepin-4-one, m.p. 181°–183°.

Following the procedures set forth in Example 2 above, from 3,5-dihydro-2-methylamino-5-phenyl-4H-1,5-benzodiazepin-4-one there can be prepared 3,5-dihydro-2-(N-nitroso-methylamino) —5-phenyl-4H-1,5-benzodiazepin-4-one, m.p. 139°–140°.

Following the procedures set forth in Example 3 above, from 3,5-dihydro-2-(N-nitrosomethyl a mino)-5-phenyl-4H-1,5-benzodiazepin-4-one there can be prepared 4,6-dihydro-1-methyl-6-phenyl-5H-S-triazolo [4,5-a][1,5] benzodiazepin-5-one, m.p. 248°–250°.

EXAMPLE 6

Preparation of 7-chloro-3,5-dihydro-2-methoxy-5-phenyl-4H-1,5-benzodiazepin-4-one A mixture of 3.3g (0.01M) of 7-chloro-3,5-dihydro-2-(N-nitrosomethylamino)-5-phenyl-4H-1,5-benzodiazepin-4-one, 5 ml of triethylamine and 50 ml. of methanol was heated to reflux for 2 hrs. The solvents were evaporated under reduced pressure and the residue was crystallized from ether/hexane to yield the above named product, m.p. 136°–138°.

EXAMPLE 7

Preparation of 8-chloro-4,6-dihydro-1-methyl-6-phenyl-5H-S-triazolo [4,5-a][1,5] benzodiazepin-5-one A mixture of 3g (0.01 M) of 7-chloro-3,5-dihydro-2-methoxy-5-phenyl-4H-1,5-benzodiazepin-4-one, 2g of acetylhydrazide and 30 ml of bis-(2-methoxyethyl) ether was heated to reflux for 3 hrs. After evaporation under reduced pressure the residue was partitioned between ether and 2N hydrochloric acid. The aqueous phase was washed with ether, made alkaline with ammonia and extracted with methylene chloride. The extracts were dried and evaporated. Crystallization from methylene chloride/ether yielded the above-named product m.p. 295°–298°.

EXAMPLE 8

Preparation of 8-chloro-4,6-dihydro-1-methyl-6-phenyl-5H-S-triazolo [4,5-a][1,5] benzodiazepin-5-one A mixture of 3.3g (0.01M) of 7-chloro-3,5-dihydro-2-(N-nitrosomethylamino)-5-phenyl-4H-1,5-benzodiazepin-4-one, 2g of acetylhydrazine, 5 ml of triethylamine and 50 ml of n-butanol was heated to reflux for 3 hrs. Half of the solvent was then removed by distillation and replaced by fresh n-butanol. Refluxing was continued for 3 days. The residue obtained after evaporation was chromatographed over 100 g of silical gel(Merck 70-230 mesh) using 10% (v/v) ethanol in methylene chloride for elution. Crystallization of the pure fraction from methylene chloride/ether yielded the above maned product, m.p. 298°–300°.

EXAMPLE 9

Pharmaceutical formulations using 8-chloro-4,6-dihydro-1-methyl-6-phenyl-5H-S-triazolo (4,5-a) benzodiazepin-5-one as the active ingredient:

| Capsule Formulation | |
|---|---|
| 8-chloro-4,6-dihydro-1-methyl-6-phenyl-5H-S-triazolo (4,5-a) benzodiazepin-5-one | 10 mg |
| Lactose | 158 mg |
| Corn Starch | 37 mg |
| Talc | 5 mg |
| | 210 mg |

PROCEDURE

1. The drug was mixed with the lactose and corn starch in a suitable mixer.
2. The mixture was further blended by passing through a Fitzpatrick Comminuting machine with a #1A screen with knives forward.
3. The blended powder was returned to the mixer, the talc added and blended thoroughly. The mixture was then filled into #4 hard shell gelatin capsules on a Parke Davis capsulating machine. (Any similar type machine may be used).

| Capsule Formulation | |
|---|---|
| 8-chloro-4,6-dihydro-1-methyl-6-phenyl-5H-S-triazolo (4,5-a) benzodiazepin-5-one | 50 mg |
| Lactose, USP | 125 mg |
| Corn Starch, USP | 30 mg |

| Capsule Formulation -continued | |
|---|---|
| Talc, USP | 5 mg |
| | 210 mg |

PROCEDURE

1. The drug was mixed with lactose and corn starch in a suitable mixer.
2. The mixture was further blended by passing through a Fitzpatrick Comminuting machine with a No. 1A screen with knives forward.
3. The blended powder was returned to the mixer, the talc added and blended thoroughly.
4. The mixture was filled into No. 4 hard shell gelatin capsules on a Parke Davis capsulating machine.

| Parenteral Formulation | | |
|---|---|---|
| 8-chloro-4,6-dihydro-1-methyl-6-phenyl-5H-S-triazolo (4,5-a) benzodiazepin-5-one | 2.0 | mg |
| Propylene Glycol | 0.4 | cc |
| Benzyl Alcohol (Benzaldehyde free) | 0.15 | cc |
| Ethanol 95 percent USP | 0.1 | cc |
| Water for Injection q.s. | 1.0 | cc |

PROCEDURE (For 10,000 cc)

1. The 20 grams of the drug were dissolved in the benzyl alcohol; 4,000 cc of propylene glycol and 1,000 cc of ethanol were added.
2. The solution was brought up to final volume of 10,000 cc with Water for Injection.
3. The solution was filtered through an 0.2 Selas candle, filled into suitable size ampuls, gassed with nitrogen and sealed.

| Tablet Formulation | Per Tablet |
|---|---|
| 8-chloro-4,6-dihydro-1-methyl-6-phenyl-5H-S-triazolo (4,5-a) benzodiazepin-5-one | 25.00 mg |
| Lactose, USP | 64.50 mg |
| Corn Starch | 10.00 mg |
| Magnesium Stearate | 0.50 mg |

PROCEDURE

1. The drug was mixed with lactose, corn starch and magnesium stearate in a suitable mixer.
2. The mixture was further blended by passing through a Fitzpatrick Comminuting machine fitted with a No. 1A screen with knives forward.
3. The mixed powders were slugged on a tablet compressing machine.
4. The slugs were comminuted to a mesh size (No. 16 screen) and mixed well.
5. The tablets were compressed at a tablet weight of 100 mg using tablet punches having a diameter of approximately ¼". (Tablets may be either flat or biconvex and may be scored if desired).

| Tablet Formulation | Per Tablet |
|---|---|
| 8-chloro-4,6-dihydro-1-methyl-6-phenyl-5H-S-triazolo (4,5-a) benzodiazepin-5-one | 10.0 mg |
| Lactose | 113.5 mg |
| Corn Starch | 70.5 mg |
| Pregelatinized Corn Starch | 8.0 mg |
| Calcium Stearate | 3.0 mg |
| | 205.0 mg |

PROCEDURE

1. The drug was mixed with the lactose, corn starch and pregelatinized corn starch in a suitable size mixer.
2. The mix was passed through a Fitzpatrick Comminuting machine fitted with No. 1A screen and with knives forward.
3. The mix was returned to the mixer and moistened with water to a thick paste. The moist mass was passed through a No. 12 screen and the moist granules were dried on paper lined trays at 110° F.
4. The dried granules were returned to the mixer, the calcium stearate was added and mixed well.
5. The granules were compressed at a tablet weight of 200 mg using standard concave punches having a diameter of 5/16".

We claim:

1. A compound of the formula

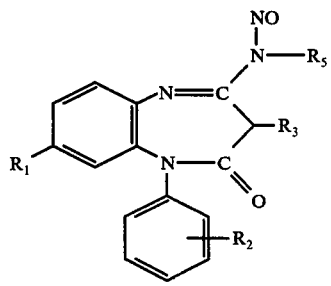

wherein $R_1$ is selected from the group consisting of hydrogen, halogen, lower alkyl, lower alkoxy, trifluoromethyl, nitro and amino; $R_2$ signifies hydrogen, halogen, or lower alkoxy; $R_3$ signifies hydrogen or lower alkyl and $R_5$ signifies lower alkyl.

* * * * *